(12) United States Patent
Song et al.

(10) Patent No.: US 11,724,155 B2
(45) Date of Patent: Aug. 15, 2023

(54) ASSISTIVE FITNESS SYSTEM AND METHOD, FITNESS EQUIPMENT

(71) Applicants: Beijing BOE Optoelectronics Technology Co., Ltd., Beijing (CN); BOE TECHNOLOGY GROUP CO., LTD., Beijing (CN)

(72) Inventors: Yubing Song, Beijing (CN); Yue Gu, Beijing (CN); Bin Ma, Beijing (CN); Mingjing Wang, Beijing (CN)

(73) Assignees: BEIJING BOE OPTOELECTRONICS TECHNOLOGY CO., LTD., Beijing (CN); BOE TECHNOLOGY GROUP CO., LTD., Beijing (CN)

( * ) Notice: Subject to any disclaimer, the term of this patent is extended or adjusted under 35 U.S.C. 154(b) by 91 days.

(21) Appl. No.: 17/558,959

(22) Filed: Dec. 22, 2021

(65) Prior Publication Data
US 2022/0111252 A1 Apr. 14, 2022

Related U.S. Application Data

(63) Continuation-in-part of application No. 16/040,261, filed on Jul. 19, 2018, now abandoned.

(30) Foreign Application Priority Data
Oct. 18, 2017 (CN) .......................... 201710971479.7

(51) Int. Cl.
G09B 19/00 (2006.01)
A63B 24/00 (2006.01)

(52) U.S. Cl.
CPC ...... *A63B 24/0006* (2013.01); *A63B 24/0062* (2013.01); *A63B 2024/0012* (2013.01);
(Continued)

(58) Field of Classification Search
CPC ............ G09B 19/0038; A63B 24/0006; A63B 24/0062
(Continued)

(56) References Cited

U.S. PATENT DOCUMENTS

2004/0254472 A1 12/2004 McQuilkin
2005/0215890 A1 9/2005 Wilson et al.
(Continued)

FOREIGN PATENT DOCUMENTS

CN 2538381 Y 3/2003
CN 201392244 Y 1/2010
(Continued)

OTHER PUBLICATIONS

Al-Nakhli, H. H., Petrofsky, J. S., Laymon, M. S., & Berk, L. S. (2012). The Use of Thermal Infra-Red Imaging to Detect Delayed Onset Muscle Soreness. Journal of Visualized Experiments, (59). doi:10.3791/3551 (Year: 2012).*
(Continued)

*Primary Examiner* — Thomas J Hong
(74) *Attorney, Agent, or Firm* — Xsensus LLP

(57) ABSTRACT

An assistive fitness system, assistive fitness method, and fitness equipment are provided. The assistive fitness system includes a thermal imaging device configured to receive an infrared signal from a human body and perform thermal imaging processing based on the infrared signal to generate a human body image; a comparing device configured to compare the human body image with a reference image of a standard fitness movement to generate a comparison result; and a display device configured to display the human body image and the comparison result of the human body image and the reference image.

11 Claims, 4 Drawing Sheets

(52) U.S. Cl.
CPC ... *A63B 2024/0068* (2013.01); *A63B 2220/05* (2013.01); *A63B 2220/13* (2013.01); *A63B 2220/20* (2013.01); *A63B 2220/806* (2013.01); *G09B 19/0038* (2013.01)

(58) Field of Classification Search
USPC ........................................................ 434/247
See application file for complete search history.

(56) References Cited

U.S. PATENT DOCUMENTS

| | | | |
|---|---|---|---|
| 2013/0116591 | A1 | 5/2013 | Heller |
| 2015/0196805 | A1* | 7/2015 | Koduri ............... A63B 24/0087 |
| | | | 482/6 |
| 2016/0156856 | A1 | 6/2016 | Lee et al. |
| 2016/0287085 | A1 | 10/2016 | Fukui et al. |
| 2018/0156667 | A1 | 6/2018 | Chrostowski |
| 2018/0315247 | A1 | 11/2018 | Van Andel |
| 2019/0077007 | A1* | 3/2019 | Mallinson ............. A61B 5/1118 |

FOREIGN PATENT DOCUMENTS

| | | |
|---|---|---|
| CN | 103390174 A | 11/2013 |
| CN | 104519787 A | 4/2015 |
| CN | 105903167 A | 8/2016 |

OTHER PUBLICATIONS

HadZié V, Sirok B, Malnergié A, Goh M. Can infrared thermography be used to monitor fatigue during exercise? A case study. J Sport Health Sci. Jan. 2019;8(1):89-92. doi: 10.1016/j.jshs.2015.08.002. Epub Nov. 4, 2015. PMID: 30719388; PMCID: PMC6349566 , available online Nov. 4, 2015. (Year: 2015).*
First Office Action for Chinese Patent Application No. 201710971479.7 dated Nov. 2, 2018.
Second Office Action for Chinese Patent Application No. 201710971479.7 dated Feb. 19, 2019.
Applicant-Initiated Interview Summary for U.S. Appl. No. 16/040,261 dated Jan. 26, 2021.
Applicant-Initiated Interview Summary for U.S. Appl. No. 16/040,261 dated Nov. 29, 2021.
Hadzic, et al., "Can infrared thermography be used to monitor fatigue during exercise?" ScienceDirect, Journal of Sport and Health Science, 2015.
Final Office Action for U.S. Appl. No. 16/040,261 dated Sep. 22, 2021.
Al-Nakhli, et al., "The Use of Thermal Infra-Red Imaging to Detect Delayed Onset Muscle Soreness", Journal of Visualized Experiments, Jan. 22, 2012.
Non-Final Office Action for U.S. Appl. No. 16/040,261 dated Jun. 4, 2021.
Final Office Action for U.S. Appl. No. 16/040,261 dated Nov. 19, 2020.
Non-Final Office Action for U.S. Appl. No. 16/040,261 dated Jun. 12, 2020.

* cited by examiner

ASSISTIVE FITNESS SYSTEM AND METHOD, FITNESS EQUIPMENT

CROSS-REFERENCE TO RELATED APPLICATION

The present application is a continuation-in-part of U.S. patent application Ser. No. 16/040,261 entitled "ASSISTIVE FITNESS SYSTEM AND METHOD, FITNESS EQUIPMENT," filed on Jul. 19, 2018, which claims the benefit of and priority to Chinese Patent Application No. 201710971479.7, filed on Oct. 18, 2017, where the contents of both of which are incorporated by reference in their entireties herein as part of the present application.

TECHNICAL FIELD

The present disclosure relates to the field of smart fitness technology and, in particular, to an assistive fitness system and method, and fitness equipment.

BACKGROUND

With widespread improvement of the quality of life, fitness has been integrated into the daily lives of most people. People can use various types of fitness equipment, such as treadmills, elliptical machines, spinning bikes, and strength training equipment, in gyms or at home, and people are paying more and more attention to the effects of fitness exercise and the safety while doing the exercise.

It should be noted that the information disclosed in the foregoing background section is only for enhancement of understanding of the background of the present disclosure and therefore may include information that does not constitute related art that is already known to those of ordinary skill in the art.

BRIEF SUMMARY

According to some arrangements, an assistive fitness system includes:
a thermal imaging device, configured to receive an infrared signal from a human body and perform thermal imaging processing based on the infrared signal to generate a human body image,
a comparing device, configured to compare the human body image with a reference image of a standard fitness movement to generate a comparison result, and
a display device, configured to display the human body image and the comparison result of the human body image and the reference image in a nested manner.

According to some arrangements, an assistive fitness method includes
receiving an infrared signal from a human body and performing thermal imaging process based on the infrared signal to generate a human body image,
comparing the human body image with a reference image of a standard fitness movement to generate a comparison result, and
displaying the human body image and the comparison result of the human body image and the reference image in a nested manner.

According to some arrangements, fitness equipment includes the assistive fitness system described above.

It should be noted that, the above general description and following detailed description are illustrative and explanatory only but not restrictive to the present disclosure.

BRIEF DESCRIPTION OF THE DRAWINGS

The accompanying drawings herein are incorporated in and constitute a part of this specification, illustrate arrangements consistent with the present disclosure, and together with the description serve to explain the principles of the present disclosure. Understandably, the drawings in the following description are merely some arrangements of the present disclosure, and those skilled in the art can also obtain other drawings based on these drawings without any creative labor.

DETAILED DESCRIPTION

Figure 1:
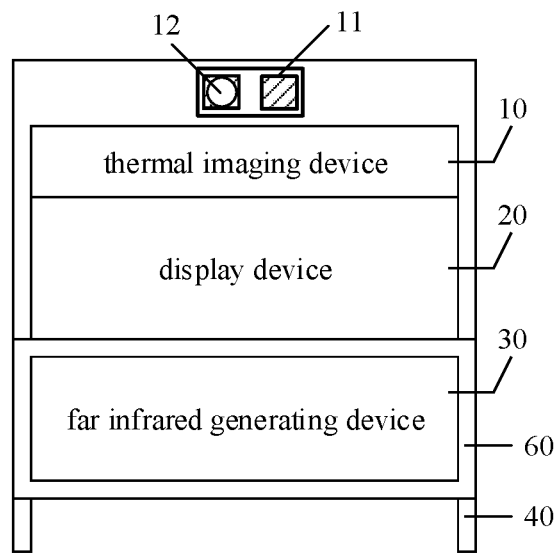
FIG. 1 schematically shows a schematic diagram of an assistive fitness system in an exemplary arrangement of the present disclosure.

Example arrangements will now be described more fully with reference to the accompanying drawings. However, example arrangements can be implemented in various forms and should not be construed as limited to the examples set forth herein; rather, these arrangements are provided so that the present disclosure will be more comprehensive and complete, and will fully convey the concept of the example arrangements to those skilled in the art. The features, structures, or characteristics described may be combined in any suitable manner in one or more arrangements.

Moreover, the drawings are merely schematic illustrations of the present disclosure and are not necessarily drawn to scale. The same reference numerals in the drawings denote the same or similar parts, and their repeated description will be omitted. Some of the block diagrams shown in the figures are functional entities and do not necessarily have to correspond to physically or logically independent entities. These functional entities may be implemented in software, or implemented in one or more hardware modules or integrated circuits, or implemented in different network and/or processor devices and/or microcontroller devices. As such, a processor can include at least one hardware processor, for example.

Figure 2:
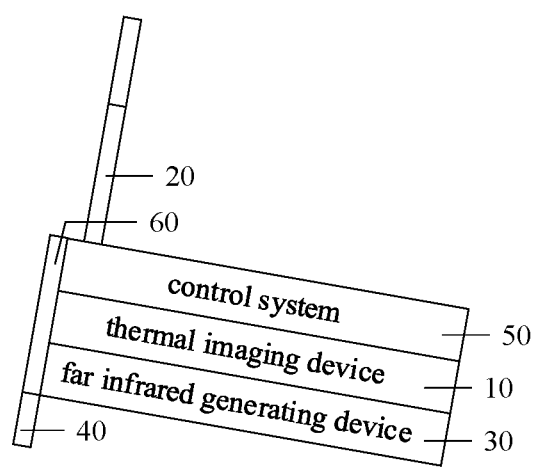
FIG. 2 schematically shows another schematic diagram of an assistive fitness system in an exemplary arrangement of the present disclosure.

The present example arrangement provides an assistive fitness system that can be placed in front of the exercise area, to collocate with the exercise equipment to assist a fitness person in exercising. As shown in FIG. 1 and FIG. 2, the assistive fitness system may include:

a thermal imaging device 10, configured to receive an infrared signal from a human body and perform thermal imaging processing based on the infrared signal to generate a human body image;

a comparing device, which may be a processor, configured to compare the human body image with a reference image of a standard fitness movement to generate a comparison result; and a display device 20, configured to display the human body image and the comparison result of the human body image and the reference image.

In this arrangement, the display device 20 can display the human body image generated by the thermal imaging process and the comparison result of the human body image and the reference image in a nested manner. That is, while the human body image is displayed, the comparison result is nested with the human body image in a line outline manner for display.

In particular, according to the embodiment, the comparison result and the human body image are displayed simultaneously, such that profile of the human body image is nested with profile of the comparison result, and thus the comparison result is shown clearly to the user. In another embodiment, the human body image and the comparison result are displayed in the nested manner by changing the profile of the human body image to show the comparison result.

In one embodiment, the assistive fitness system may further include a camera 12 configured to obtain an image of the user; and a distance sensor 11 configured to acquire a first distance between the user and the display device. In the embodiment, the processor is further configured to determine, from the image of the user and the first distance, position coordinates of a target position at which the user is gazing in a preset coordinate system, where the preset coordinate system is located in association with the human body. The display device 20 is further configured to display the human body image and the comparison result in the nested manner at the target position.

In particular, the camera 12 is configured to obtain a first image of the user looking straight at the display device and a second image of the user gazing at a target position. The processor is further configured to determine the position coordinates of the target position in the preset coordinate system based on the first image, the second image, and the first distance. More particularly, the processor is further configured to: identify a first center of a left-eye pupil and a first center of a right-eye pupil in the first image; identify a second center of the left-eye pupil or a second center of the right-eye pupil in the second image; and determine a position abscissa of the target position in the preset coordinate system based on a first angle, a second distance between the first center of the left-eye pupil and the first center of the right-eye pupil in a preset horizontal direction, and the first distance. The first angle is a deflection angle between the first center of the left-eye pupil and the second center of the left-eye pupil in the preset horizontal direction, or, a deflection angle between the first center of the right-eye pupil and the second center of the right-eye pupil in the preset horizontal direction. The processor is further configured to determine a position ordinate of the target position in the preset coordinate system based on a second angle, the second distance, and the first distance. The second angle is a deflection angle between the first center of the left-eye pupil and the second center of the left-eye pupil in a preset vertical direction, or, a deflection angle between the first center of the right-eye pupil and the second center of the right-eye pupil in the preset vertical direction. An origin of the preset coordinate system is a central position between the first center of the left-eye pupil and the first center of the right-eye pupil, and the preset vertical direction is perpendicular to the preset horizontal direction.

The exemplary arrangement is not limited thereto. The display device 20 may include any one of an LCD (Liquid Crystal Display), an OLED (Organic Light Emitting Diode), and a PDP (Plasma Display Panel), but the disclosure is not limited to these examples.

It should be noted that the thermal imaging device 10 may be an integrated device or may be a device composed of a plurality of components. In one arrangement, the thermal imaging device 10 shown in FIG. 1 may be a receiving unit for receiving an infrared signal, and the thermal imaging device 10 shown in FIG. 2 may be a processing unit for performing thermal imaging processing. The infrared signal received by the receiving unit can be sent to the processing unit for processing by wired or wireless communication. The present disclosure does not limit the specific arrangement and position of the thermal imaging device 10.

In the assistive fitness system provided by the exemplary arrangement of the present disclosure, by adding a thermal imaging device, a comparison device, and a display device, thermal imaging processing may be performed on a fitness person, to generate a corresponding human body image and compare the human body image with a reference image of a standard fitness movement, so as to present the comparison result in the display device. In this way, the fitness person can not only observe whether his own movement is standard through the comparison result presented by the display device, but also can observe a movement state of the muscle so as to avoid physical injury caused by wrong movement or excessive exercise.

The assistive fitness system provided in this exemplary arrangement will be described in detail below with reference to the accompanying drawings.

Figure 3:
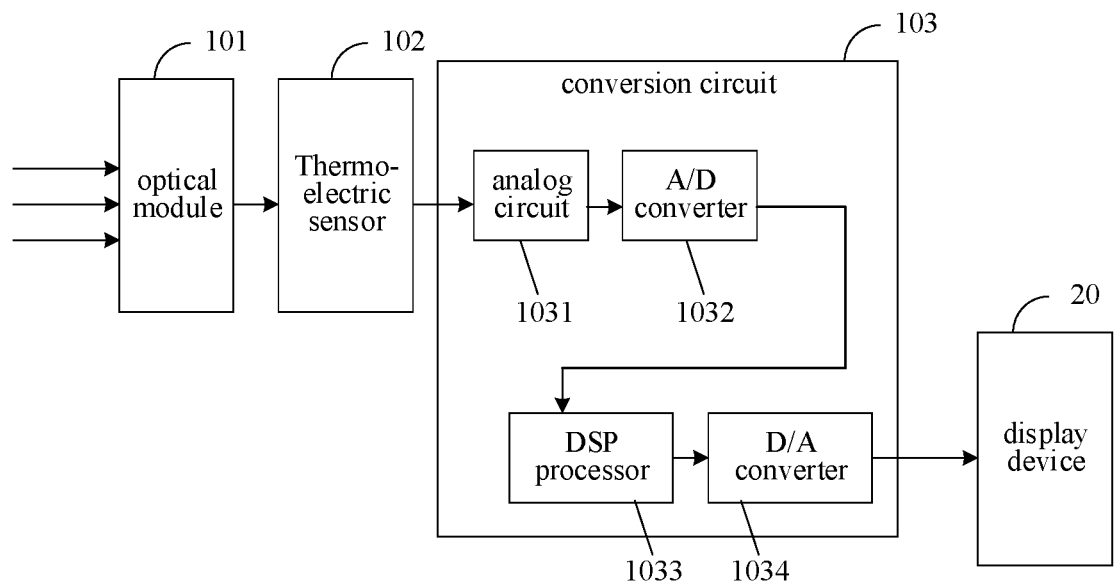
FIG. 3 schematically shows a schematic diagram of a thermal imaging device in an exemplary arrangement of the present disclosure.

In this exemplary arrangement, as shown in FIG. 3, the thermal imaging apparatus 10 may include:

an optical module 101 configured to receive an infrared signal from a human body and focus the infrared signal to a focal plane of the optical module 101;

a thermoelectric sensor 102 disposed at a position of the focal plane and configured to extract a thermal signal in the infrared signal and convert the thermal signal into an electrical signal; and a conversion circuit 103 connected to the thermoelectric sensor 102 and configured to acquire the electrical signal and process the electrical signal to convert the electrical signal into an image signal.

In the arrangement, the conversion circuit 103 may include an analog circuit 1031, an A/D (Analog-to-Digital) converter 1032, a digital signal processor (DSP) 1033, and a D/A (Digital-to-Analogue) converter 1034 successively connected.

In this way, the infrared signal radiated by the fitness person is received by the optical module 101 and focused on the thermoelectric sensor 102 located at the focal plane. The thermoelectric sensor 102 extracts a thermal signal in the infrared signal and converts the thermal signal into an electrical signal for transmission to the conversion circuit 103. The analog circuit 1031 in the conversion circuit 103 acquires the above electrical signal and performs processing such as amplification and noise removal, and then converts it into a signal that can be acquired by the A/D converter 1032. Then, through the A/D converter 1032, the analog signal is converted into a digital signal for transmission to the DSP processor 1033 for image processing. The processed digital signal is then transmitted to the D/A converter 1034 to be converted into an analog signal, and the converted analog signal is finally presented on the display device 20 for human viewing.

It should be noted that the thermoelectric sensor 103 may be a pyroelectric sensor or a general thermoelectric sensor.

Figure 4:
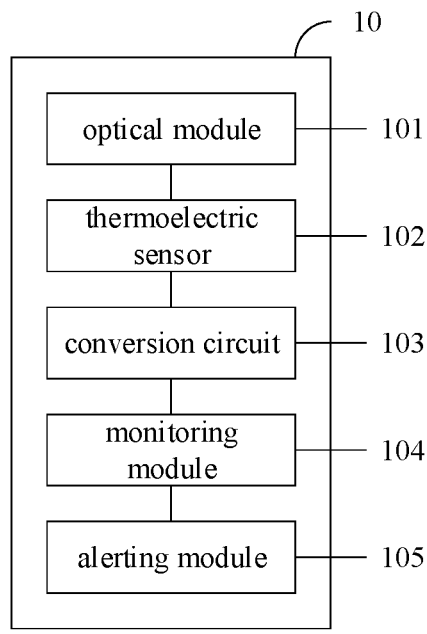
FIG. 4 schematically shows a schematic diagram of a thermal imaging device in an exemplary arrangement of the present disclosure.

In this exemplary arrangement, as shown in FIG. 4, the thermal imaging apparatus 10 may further include:

a monitoring module 104 configured to monitor a muscle state of the human body in real time and judge whether a current muscle state reaches an exercise saturation state automatically; and an alerting module 105 connected to the monitoring module 104 and configured to issue an alert when the current muscle state reaches the exercise saturation state.

In this way, the thermal imaging device 10 can determine the muscle state of the fitness person in real time, and issues a prompt when reaching an exhausted or saturated state, so that it can effectively prevent muscle strain and even more serious damage caused by excessive exercise.

In the present exemplary arrangement, the assistive fitness system may further include a communication device, connected to the display device 200, and configured to acquire a reference image of the standard fitness movement for transmission to the display device 20.

In this case, the display device 20 may include the display device includes a first display area and a second display area. The first display area may be used to display a human body image generated through the thermal imaging process and a comparison result of the human body image and the reference image. The second display area may be used to display the reference image of the standard fitness movement.

In one arrangement, the first display area and the second display area can be set to be left and right side by side, so that the fitness person can compare his own movement with the standard fitness movement to timely correct the wrong movement.

Based on the above arrangements, referring to FIG. 1 and FIG. 2, the assistive fitness system may further include:

a far infrared generating device 30 configured to generate a far infrared light and irradiate to the human body, so that resonance absorption occurs in the human body; and a bracket 40 configured to adjust a height of the far infrared generating device 30, so that the human body is located in a far infrared imaging area of the far infrared generating device 30.

In the arrangement, the far infrared light generated by the far infrared generating device 30 has a wavelength range greater than or equal to 4 μm.

It should be noted that the resonance absorption means that a frequency of the far infrared light generated by the far infrared generating device 30 is close to a vibration frequency of cellular molecules in the human body, and thus is easily absorbed by the human body to generate a resonance phenomenon. In the present arrangement, the infrared wavelength of natural radiation of the human body is about 10 μm, and the far infrared light greater than or equal to 4 μm is generated by the far infrared generating device 30, which is advantageous for the resonance absorption of the human body. In another arrangement, when the far infrared light generated by the far infrared generating device 30 has a wavelength of 9.4 μm, the resonance absorption occurred in the human body achieves an optimum effect.

In this way, the resonance absorption may occur due to the far infrared light illuminating the human body, and on one hand, substances which are likely to cause fatigue and aging, such as lactic acid, free fatty acid, cholesterol, excess subcutaneous fat, etc., may be metabolized directly at the skin without using kidney by the activity of the follicular orifice and under subcutaneous fat, thereby alleviating the fatigue caused by exercise and effectively prolonging the exercise time; on the other hand, the oxygen content of the blood can be increased, thereby improving the efficiency of aerobic exercise; on another hand, the heat energy in the body can also be improved, in order to activate the cells, thereby promoting the metabolism and combustion decomposition of the adipose tissue, in order to consume excess fat.

Based on this, the assistive fitness system may further include a control system 50 in communication with the bracket 40, for automatically controlling the lifting and lowering of the bracket 40.

Further, the assistive fitness system may further include a housing 60 disposed above the bracket 40 and connected to the bracket 40 for placing the thermal imaging device 10, the display device 20, the far infrared generating device 30, or the like. In this way, by adjusting the height of the housing 60, the bracket 40 may adjust the height of the far infrared generating device 30.

Figure 5:
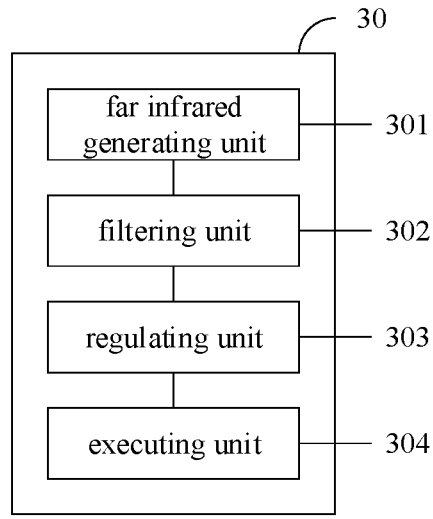
FIG. 5 schematically shows a schematic diagram of a far infrared generating device in an exemplary arrangement of the present disclosure.

In this exemplary arrangement, as shown in FIG. 5, the far infrared generating device 30 may include:

a far infrared generating unit 301 configured to generate a far infrared light with a wavelength greater than or equal to 1 μm;

a filtering unit 302 configured to perform filter processing on the far infrared light, so as to control the wavelength of the far infrared light to be greater than or equal to 4 μm;

a regulating unit 303 configured to perform energy regulation on the far infrared light; and an executing unit 304 configured to apply the far infrared light subjected to the filter processing and the energy regulation to the human body, so as to achieve an assistive fitness effect.

Based on this, it can be seen that the far infrared light ultimately acting on the human body has a band and energy suitable for reception by the human body. Such far infrared light irradiating to the human body can at least achieve following effects: first, expanding microvessels, promoting blood circulation, rejuvenating enzymes, and strengthening blood and cell tissue metabolism; second, relaxing muscles, driving exchange of oxygen and nutrient in microvascular networks, and eliminating fatigue and aging substances accumulated in the body to remove internal swelling; and third, increasing blood oxygen content. In this way, by generating suitable far infrared light to illuminate the human body, the present arrangement can not only prolong the exercise time significantly, but also accelerate the exercise consumption and keep body healthy.

Figure 6:
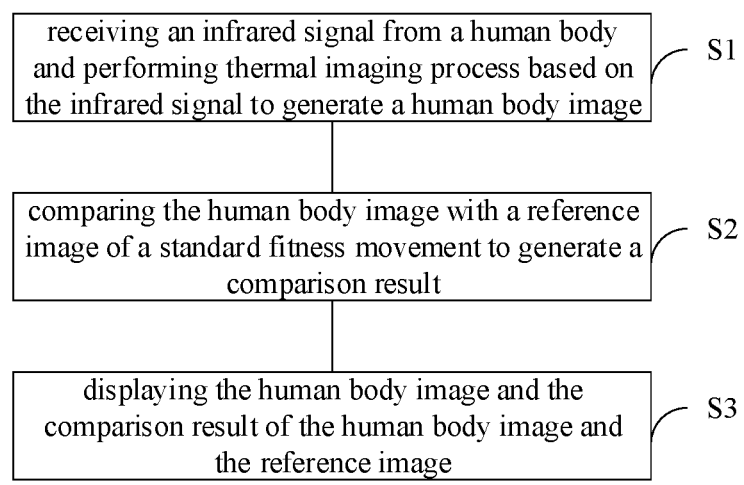
FIG. 6 schematically showing a flow chart of an assistive fitness method in an exemplary arrangement of the present disclosure.

The example arrangement also provides an assistive fitness method. As shown in FIG. 6, the assistive fitness method may include:

S1, receiving an infrared signal from a human body and performing thermal imaging process based on the infrared signal to generate a human body image;

S2, comparing the human body image with a reference image of a standard fitness movement to generate a comparison result; and S3, displaying the human body image and the comparison result of the human body image and the reference image.

In the assistive fitness method provided by the exemplary arrangement of the present disclosure, thermal imaging processing may be performed on a fitness person, to generate a corresponding human body image and compare the human body image with a reference image of a standard fitness movement, so as to present the comparison result in the display device. In this way, the fitness person can not only observe whether his own movement is standard through the comparison result presented by the display device, but also can observe a movement state of the muscle, so as to avoid physical injury caused by wrong movement or excessive exercise.

Figure 7:
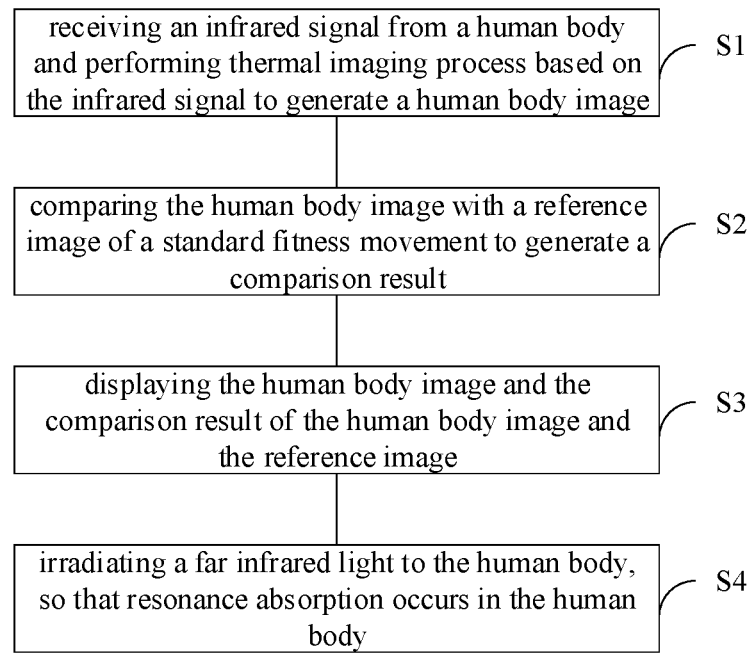
FIG. 7 schematically showing another flow chart of an assistive fitness method in an exemplary arrangement of the present disclosure.

In this exemplary arrangement, as shown in FIG. 7, the assistive fitness method may further include:

S4, irradiating a far infrared light to the human body, so that resonance absorption occurs in the human body.

In this way, the resonance absorption may occur due to the far infrared light illuminating the human body, and on one hand, substances which are likely to cause fatigue and aging, such as lactic acid, free fatty acid, cholesterol, excess subcutaneous fat, etc., may be metabolized directly at the skin without using kidney by the activity of the follicular orifice and under subcutaneous fat, thereby alleviating the fatigue caused by exercise and effectively prolonging the exercise time; on the other hand, the oxygen content of the blood can be increased, thereby improving the efficiency of aerobic exercise; on another hand, the heat energy in the body can also be improved, in order to activate the cells, thereby promoting the metabolism and combustion decomposition of the adipose tissue, in order to consume excess fat.

It should be noted that specific details of the assistive fitness method have been described in detail in the corresponding assistive fitness system, and will not be repeated here.

Based on this, the present exemplary arrangement further provides a fitness equipment including the above-mentioned assistive fitness system. In the arrangement, the assistive fitness system is arranged in front of the exercise area and can collocate with the exercise equipment to assist a fitness person in exercising.

In one arrangement, the assistive fitness system may be disposed directly in front of the treadmill, and the far infrared generating device 30 may be adjusted to an appropriate height by controlling the lifting and lowering of the bracket 40, so as to ensure that the human body is located in the far infrared imaging area of the far infrared generating device 30.

It should be noted that although several modules or units of the apparatus for action execution are mentioned in the above detailed description, such division is not mandatory. In fact, according to arrangements of the present disclosure, features and functions of two or more modules or units described above may be embodied in one module or unit. Conversely, the features and functions of one module or unit described above may be further divided into a plurality of modules or units for embodying.

Moreover, although various steps of the method in the present disclosure have been described in a specific order in the drawings, this does not require or imply that these steps must be performed in this particular order, or all illustrated steps must be performed to achieve the desired result. Additionally or alternatively, some steps may be omitted, multiple steps may be combined into one step, and/or one step may be broken down into multiple steps for executions.

Those skilled in the art will readily recognize other arrangements of the disclosure after considering the specification and practicing the disclosure disclosed herein. This application is intended to cover any variations, uses, or adaptations of the present disclosure which follow the general principles of the present disclosure and include any common knowledge or conventional techniques in this technical field not disclosed by the present disclosure. The specification and arrangements are to be regarded as illustrative only, with true scope and spirit of the disclosure indicated by the claims.

It should be understood that the present disclosure is not limited to the precise structure that has been described above and shown in the drawings, and various modifications and changes can be made without departing from the scope thereof. The scope of the present disclosure is limited only by the appended claims.

Therefore, the following is claimed:

1. An assistive fitness system, comprising:
a thermal imaging device configured to receive an infrared signal from a human body of a user and perform thermal imaging processing based on the infrared signal to generate a human body image;
a processor configured to compare the human body image with a reference image of a standard fitness movement to generate a comparison result; and
a display device configured to display the human body image and the comparison result of the human body image and the reference image in a nested manner,
wherein the assistive fitness system further comprises:
a camera configured to obtain an image of the user; and
a distance sensor configured to acquire a first distance between the user and the display device, wherein:
the processor is further configured to determine, from the image of the user and the first distance, position coordinates of a target position at which the user is gazing in a preset coordinate system, the preset coordinate system being located in association with the human body; and
the display device is further configured to display the human body image and the comparison result in the nested manner at the target position,
wherein the camera is configured to obtain a first image of the user looking straight at the display device and a second image of the user gazing at a target position; and the processor is further configured to determine the position coordinates of the target position in the preset coordinate system based on the first image, the second image, and the first distance, and
wherein the processor is further configured to:
identify a first center of a left-eye pupil and a first center of a right-eye pupil in the first image;
identify a second center of the left-eye pupil or a second center of the right-eye pupil in the second image;
determine a position abscissa of the target position in the preset coordinate system based on a first angle, a second distance between the first center of the left-eye pupil and the first center of the right-eye pupil in a preset horizontal direction, and the first distance, wherein the first angle is a deflection angle between the first center of the left-eye pupil and the second center of the left-eye pupil in the preset horizontal direction, or, a deflection angle between the first center of the right-eye pupil and the second center of the right-eye pupil in the preset horizontal direction; and
determine a position ordinate of the target position in the preset coordinate system based on a second angle, the second distance and the first distance, wherein the second angle is a deflection angle between the first center of the left-eye pupil and the second center of the left-eye pupil in a preset vertical direction, or, a deflection angle between the first center of the right-eye pupil and the second center of the right-eye pupil in the preset vertical direction, wherein:
an origin of the preset coordinate system is a central position between the first center of the left-eye pupil and the first center of the right-eye pupil; and the preset vertical direction is perpendicular to the preset horizontal direction.

2. The assistive fitness system of claim 1, wherein the display device is configured to display the comparison result and the human body image simultaneously, such that profile of the human body image is nested with profile of the comparison result.

3. The assistive fitness system of claim 1, wherein the human body image and the comparison result are displayed in the nested manner by changing the profile of the human body image to show the comparison result.

4. The assistive fitness system of claim 1, wherein the thermal imaging device comprises:
an optical assembly configured to receive the infrared signal from the human body and focus the infrared signal to a focal plane of the optical assembly;
a thermoelectric sensor disposed at a position of the focal plane and configured to extract a thermal signal in the infrared signal and convert the thermal signal into an electrical signal; and
a conversion circuit connected to the thermoelectric sensor and configured to acquire the electrical signal and process the electrical signal to convert the electrical signal into an image signal.

5. The assistive fitness system of claim 1, wherein the display device comprises a first display area and a second display area, the first display area is configured to display the human body image and the comparison result, and the second display area is configured to display the reference image of the standard fitness movement.

6. An assistive fitness method, comprising:
receiving an infrared signal from a human body and performing a thermal imaging process based on the infrared signal to generate a human body image;
comparing the human body image with a reference image of a standard fitness movement to generate a comparison result; and
displaying the human body image and the comparison result of the human body image and the reference image in a nested manner,
wherein the method further comprises:
obtaining, by a camera, an image of the user;
acquiring, by a distance sensor, a first distance between the user and a display device displaying the human body image and the comparison result;
determining, from the image of the user and the first distance, position coordinates of a target position at which the user is gazing in a preset coordinate system, the preset coordinate system being located in association with the human body; and
displaying the human body image and the comparison result in the nested manner at the target position,
wherein: obtaining, by the camera, the image of the user comprises obtaining a first image of the user looking straight at the display device and a second image of the user gazing at a target position; and the method further comprises determining the position coordinates of the target position in the preset coordinate system based on the first image, the second image, and the first distance, and
wherein determining the position coordinates of the target position in the preset coordinate system based on the first image, the second image, and the first distance comprises:
identifying a first center of a left-eye pupil and a first center of a right-eye pupil in the first image;
identifying a second center of the left-eye pupil or a second center of the right-eye pupil in the second image;
determining a position abscissa of the target position in the preset coordinate system based on a first angle, a second distance between the first center of the left-eye pupil and the first center of the right-eye pupil in a preset horizontal direction, and the first distance, wherein the first angle is a deflection angle between the first center of the left-eye pupil and the second center of the left-eye pupil in the preset horizontal direction, or, a deflection angle between the first center of the right-eye pupil and the second center of the right-eye pupil in the preset horizontal direction; and
determining a position ordinate of the target position in the preset coordinate system based on a second angle, the second distance and the first distance, wherein the second angle is a deflection angle between the first center of the left-eye pupil and the second center of the left-eye pupil in a preset vertical direction, or, a deflection angle between the first center of the right-eye pupil and the second center of the right-eye pupil in the preset vertical direction;
wherein an origin of the preset coordinate system is a central position between the first center of the left-eye pupil and the first center of the right-eye pupil; and
the preset vertical direction is perpendicular to the preset horizontal direction.

7. The assistive fitness method of claim 6, wherein the displaying the human body image and the comparison result of the human body image and the reference image in a nested manner comprises displaying the comparison result and the human body image simultaneously, such that profile of the human body image is nested with profile of the comparison result.

8. The assistive fitness method of claim 6, wherein the human body image and the comparison result are displayed in the nested manner by changing the profile of the human body image to show the comparison result.

9. A fitness equipment, comprising:
an assistive fitness system, wherein the assistive fitness system comprises:
a thermal imaging device configured to receive an infrared signal from a human body and perform thermal imaging processing based on the infrared signal to generate a human body image;
a processor configured to compare the human body image with a reference image of a standard fitness movement to generate a comparison result; and
a display device configured to display the human body image and the comparison result of the human body image and the reference image in a nested manner,
wherein the assistive fitness system further comprises:
a camera configured to obtain an image of the user; and
a distance sensor configured to acquire a first distance between the user and the display device, wherein:
the processor is further configured to determine, from the image of the user and the first distance, position coordinates of a target position at which the user is gazing in a preset coordinate system, the preset coordinate system being located in association with the human body; and
the display device is further configured to display the human body image and the comparison result in the nested manner at the target position,
wherein the camera is configured to obtain a first image of the user looking straight at the display device and a second image of the user gazing at a target position; and the processor is further configured to determine the position coordinates of the target position in the preset coordinate system based on the first image, the second image, and the first distance, and wherein the processor is further configured to:

identify a first center of a left-eye pupil and a first center of a right-eye pupil in the first image;

identify a second center of the left-eye pupil or a second center of the right-eye pupil in the second image;

determine a position abscissa of the target position in the preset coordinate system based on a first angle, a second distance between the first center of the left-eye pupil and the first center of the right-eye pupil in a preset horizontal direction, and the first distance, wherein the first angle is a deflection angle between the first center of the left-eye pupil and the second center of the left-eye pupil in the preset horizontal direction, or, a deflection angle between the first center of the right-eye pupil and the second center of the right-eye pupil in the preset horizontal direction; and determine a position ordinate of the target position in the preset coordinate system based on a second angle, the second distance and the first distance, wherein the second angle is a deflection angle between the first center of the left-eye pupil and the second center of the left-eye pupil in a preset vertical direction, or, a deflection angle between the first center of the right-eye pupil and the second center of the right-eye pupil in the preset vertical direction, wherein:

an origin of the preset coordinate system is a central position between the first center of the left-eye pupil and the first center of the right-eye pupil; and the preset vertical direction is perpendicular to the preset horizontal direction.

10. The fitness equipment of claim 9, wherein the display device is configured to display the comparison result and the human body image simultaneously, such that profile of the human body image is nested with profile of the comparison result.

11. The fitness equipment of claim 9, wherein the human body image and the comparison result are displayed in the nested manner by changing the profile of the human body image to show the comparison result.

* * * * *